United States Patent
Aida et al.

(10) Patent No.: US 6,440,400 B1
(45) Date of Patent: Aug. 27, 2002

(54) TRIMETHYLCYLOHEXANE DERIVATIVES AND MELANIN-FORMATION INHIBITORS AND PERFUMEHOLDING AGENTS WITH THE USE OF THE SAME

(75) Inventors: Takashi Aida; Hiroyuki Matsuda; Kenya Ishida; Tetsuro Yamasaki; Eiko Tamai; Kazuhiko Tokoro, all of Hiratsuka (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/601,508
(22) PCT Filed: Feb. 1, 1999
(86) PCT No.: PCT/JP99/00412
§ 371 (c)(1),
(2), (4) Date: Aug. 2, 2000
(87) PCT Pub. No.: WO99/38826
PCT Pub. Date: Aug. 5, 1999

(30) Foreign Application Priority Data

Feb. 2, 1998 (JP) .............................................. 10-33550

(51) Int. Cl.[7] .............................. A61K 7/42; A61K 7/46; C07C 35/08
(52) U.S. Cl. ............................... 424/59; 424/59; 512/2; 512/8; 512/25; 512/26; 512/27; 568/822
(58) Field of Search .......................... 568/822; 424/401, 424/59; 5121/2, 8, 25–27

(56) References Cited

U.S. PATENT DOCUMENTS

| 4,252,986 A | 2/1981 | Klein et al. ................. 568/822 |
| 4,313,855 A | 2/1982 | Klein et al. ................. 252/522 |
| 4,623,750 A | 11/1986 | Schulte-Elte et al. ........ 568/822 |
| 4,711,875 A | 12/1987 | Schulte-Elte et al. .......... 512/1 |
| 5,250,512 A | 10/1993 | Ohmoto et al. ................ 512/22 |
| 5,420,098 A | 5/1995 | Ansai et al. ................. 504/133 |
| 6,054,426 A | 4/2000 | Schulte-Elte et al. ......... 512/22 |

FOREIGN PATENT DOCUMENTS

| JP | 54-117439 A | 9/1979 |
| JP | 60-6657 A | 1/1985 |
| JP | 08-73334 A | 3/1996 |
| JP | 08-73335 A | 3/1996 |
| JP | 08-73336 A | 3/1996 |
| JP | 08-73359 A | 3/1996 |
| JP | 08-198747 A | 8/1996 |
| JP | 8-333234 A | 12/1996 |

*Primary Examiner*—Jose' G. Dees
*Assistant Examiner*—Marina Lamm
(74) *Attorney, Agent, or Firm*—Kubovcik & Kubovcik

(57) ABSTRACT

The present invention is a trimethylcyclohexane derivative represented by Formula (1):

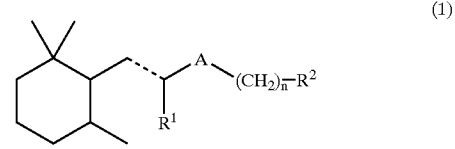

(1)

wherein A represents C=O or CH—OH, n represents 2, $R^1$ represents hydrogen or a methyl group, $R^2$ represents a straight or branched, saturated or unsaturated hydrocarbon group having 3 to 10 carbon atoms, and a dotted line represents a saturated or unsaturated carbon-carbon bond, a melanin production inhibitor and a fragrance fixative comprising one or more of the trimethylcyclohexane derivatives, and a dermal formulation comprising one or more of the melanin production inhibitors and/or fragrance fixatives.

15 Claims, No Drawings

TRIMETHYLCYLOHEXANE DERIVATIVES AND MELANIN-FORMATION INHIBITORS AND PERFUMEHOLDING AGENTS WITH THE USE OF THE SAME

This application is a 371 of PCT/JP99/00412 Feb. 1, 1999.

BACKGROUND OF THE INVENTION

1. Field of the Invention

The present invention relates to a novel trimethylcyclohexane derivative and a melanin production inhibitor and/or a fragrance fixative comprising this trimethylcyclohexane derivative as a main component, as well as a dermal formulation comprising these melanin production inhibitor and/or a fragrance fixative.

2. Description of the Related Art

An irradiation of a ray such as UV light to skin causes a sunburn and a change in the color of the skin tissue into black as a result of the production and the deposition of melanin in a chromatophore which is triggered by a irritative effect of the exposure to the UV or a hormone and the like. Freckles and liver spots reflect the fixative and the deposition of melanin throughout the entire layer of a local epidermis.

Such melanin synthesis in a epidermis is believed to be attributable to melanin production as a result of an oxidative polymerization of a tyrosine catalyzed by a tyrosinase which is an oxidase biosynthesized in a chromatophore.

An inhibition of the process of such melanin production and deposition is an aim of the development of a whitening agent and has been a subject in various studies.

The effect of vitamin C, cysteine, kojic acid, arbutin, glutathione, hydroquinone or an extract from a naturally occurring material as a substance capable of inhibiting tyrosinase activity and thus suppressing melanin production and as a substance capable of decoloring and whitening melanin once produced has already been established. Nevertheless, none of these substances is satisfactory in terms of stability, safety and odor, and has a sufficient whitening effect, and no satisfactory whitening agent has been obtained.

Other compounds having melanin production inhibiting effects which have been reported are tetrahydroionol and derivatives thereof (JP-A-8-73334, JP-A-8-73335, JP-A-8-73336 and JP-A-8-73359) and β-ionone and a dihydro form thereof (JP-A-8-198747). However, the melanin production inhibiting effect of any of these compounds is not satisfactory. In addition, their relatively intense odors pose a requirement of an effort to reduce the adverse effect on the fragrance of a final product.

Also known are the trimethylcyclohexane derivatives represented by Formula (3) and Formula (4):

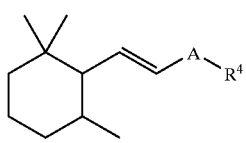

(3)

wherein A represents C=O or CH—OH, $R^4$ represents ethyl, n-propyl and isobutyl, and,

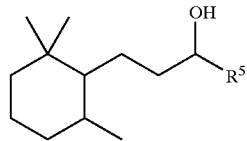

(4)

wherein $R^5$ represents ethyl, n-propyl, n-butyl and isobutyl.

A compound of Formula (3) is described only as an intermediate or a by-product in synthesizing a fragrance compound, 1-alkyl-substituted-3-(2',2',6'-trimethylcyclohexan-1-yl)propan-1-ol (JP-B-3-80780, JP-A-4-226930), while a compound of Formula (4) is described only as a fragrance (JP-A-4-21642, JP-B-7-25709). Since any of the compounds described is an intensely fragrant substance, it can not be used as a fragrance fixative. None of the publications described above contain an inhibitory effect on melanin production by a viable chromatophore.

On the other hand, a conventional method for formulating fragrant substances to prepare an excellent fragrance composition involves an incorporation of various fixatives which adjust the aroma profile and the fixative of a fragrant substance into a fragrance for the purpose of sustaining an intended fragrance.

Those employed typically are dipropylene glycol, triethyl citrate, benzyl benzoate and the like, but these fixatives do not have satisfactory fixative effects.

SUMMARY OF THE INVENTION

An objective of the invention is to provide a novel trimethylcyclohexane derivative useful as a melanin production inhibitor or as a fragrance fixative. Another object of the invention is to provide a melanin production inhibitor and/or a fragrance fixative comprising this trimethylcyclohexane derivative as a main component. Still another object of the invention is to provide a dermal formulation comprising such melanin production inhibitor and/or fragrance fixative.

The inventors made an effort to solve the problems encountered currently as discussed above and finally discovered that a novel trimethylcyclohexane derivative represented by Formula (1):

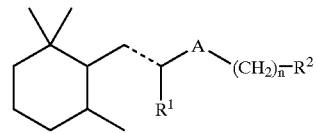

(1)

wherein A represents C=O or CH—OH, n represents 2, $R^1$ represents hydrogen or a methyl group, $R^2$ represents a straight or branched, saturated or unsaturated hydrocarbon group having 3 to 10 carbon atoms, and a dotted line represents a saturated or unsaturated carbon-carbon bond, can solve the problems, thus establishing the invention.

Thus, the inventors discovered that Compound (1) represented by Formula (1) shown above has a potent inhibitory effect on melanin production by a viable chromatophore, that a melanin production inhibitor consisting of Compound (1) is excellent in terms of stability and safety and can exhibit an extremely higher melanin production inhibiting effect when compared with a conventional product, that Compound (1) has an ability of sustaining the fragrant component of a fragrance for a prolonged period and that a fragrance fixative consisting of Compound (1) can promote the intended aroma characteristics and the fragrance fixative markedly.

In addition, it was also discovered that Compound (1) which is odorless itself does not exert any influence on the smell of a dermal formulation containing it and is stable and safe in a formulation or a base, and has an excellent melanin production inhibiting effect and an excellent fragrance fixative effect.

A novel trimethylcyclohexane derivative (1) represented by the above Formula (1), a melanin production inhibitor and/or a fragrance fixative comprising this compound, and a dermal formulation comprising such melanin production inhibitor and/or a fragrance fixative are described below.

(1) A trimethylcyclohexane derivative represented by Formula (1):

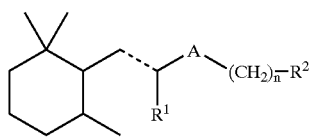

(1)

wherein A represents C=O or CH—OH, n represents 2, $R^1$ represents hydrogen or a methyl group, $R^2$ represents a straight or branched, saturated or unsaturated hydrocarbon group having 3 to 10 carbon atoms, and a dotted line represents a saturated or unsaturated carbon-carbon bond.

(2) A trimethylcyclohexane derivative wherein $R^2$ in Formula (1) according to Section (1) described above is selected from the group consisting of n-propyl, n-butyl, n-pentyl, n-hexyl, n-heptyl, isopropyl, isobutyl, sec-butyl, tert-butyl, allyl, 1-propenyl, isopropenyl, 1-butenyl, 2-butenyl, 3-butenyl, 2-methyl-l-propenyl, 2-methyl-2-propenyl, 1-ethyl-1-ethenyl, 1-methyl-1-propenyl, 1-methyl-2-propenyl, 2,6-dimethylheptyl, 2,6-dimethyl-1-heptenyl, 2,6-dimethyl-5-heptenyl and 2,6-dimethyl-1,5-heptadienyl groups.

(3) A trimethylcyclohexane derivative wherein $R^2$ in Formula (1) according to Section (1) described above is selected from the group consisting of n-propyl, n-butyl, isopropyl, isobutyl, sec-butyl, tert-butyl, allyl, 1-propenyl, isopropenyl, 1-butenyl, 2-butenyl, 3-butenyl, 2-methyl-1-propenyl, 2-methyl-2-propenyl, 1-ethyl-1-ethenyl, 1-methyl-1-propenyl and 1-methyl-2-propenyl groups.

(4) A melanin production inhibitor comprising one or more of trimethylcyclohexane derivatives according to Sections (1) to (3) described above.

(5) A fragrance fixative comprising one or more of trimethylcyclohexane derivatives according to Sections (1) to (3) described above.

(6) A dermal formulation comprising one or more melanin production inhibitors and/or fragrance fixatives according to Sections (4) to (5) described above.

(7) A melanin production inhibitor comprising one or more trimethylcyclohexane derivatives represented by Formula (2):

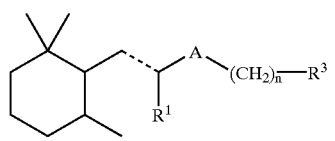

(2)

wherein A represents C=O or CH—OH, n represents 0, $R^1$ represents hydrogen or a methyl group, R3 represents a straight or branched, saturated or unsaturated hydrocarbon group having 2 to 4 carbon atoms, and a dotted line represents a saturated or unsaturated carbon-carbon bond.

(8) A dermal formulation comprising one or more melanin production inhibitors according to Section (7) described above.

The present invention is described in further detail below.

$R^2$ in Compound (1) of the invention may be, for example selected from, but is not limited to, n-propyl, n-butyl, n-pentyl, n-hexyl, n-heptyl, n-octyl, n-nonyl, n-decyl, isopropyl, isobutyl, sec-butyl, tert-butyl, isopentyl, neopentyl, 4-methylpentyl, 5-methylhexyl, 6-methylheptyl, 7-methyloctyl, 8-methylnonyl, 1-methylbutyl, 1-methylpentyl, 1-methylhexyl, 1-methylheptyl, 1-methyloctyl, 1-methylnonyl, 2,6-dimethylheptyl, allyl, 1-propenyl, 1-butenyl, 2-butenyl, 3-butenyl, 4-pentenyl, 5-hexenyl, 6-heptenyl, 7-octenyl, 8-nonenyl, 9-decenyl, 1-pentenyl, 1-hexenyl, 1-heptenyl, 1-octenyl, 1-nonenyl, 1-decenyl, isopropenyl, 2-methyl-1-propenyl, 2-methyl-2-propenyl, 1-ethyl-1-ethenyl, 1-methyl-1-propenyl, 1-methyl-2-propenyl, 3-methyl-2-butenyl, 4-methyl-3-pentenyl, 5-methyl-4-hexenyl, 6-methyl-5-heptenyl, 7-methyl-6-octenyl, 8-methyl-7-nonenyl, 2,6-dimethyl-5-heptenyl, 2,6-dimethyl-1-heptenyl, 2,6-dimethyl-1,5-heptadienyl groups and the like.

Preferably, $R^2$ is n-propyl, n-butyl, n-pentyl, n-hexyl, n-heptyl, isopropyl, isobutyl, sec-butyl, tert-butyl, allyl, 1-propenyl, isopropenyl, 1-butenyl, 2-butenyl, 3-butenyl, 2-methyl-1-propenyl, 2-methyl-2-propenyl, 1-ethyl-1-ethenyl, 1-methyl-1-propenyl, 1-methyl-2-propenyl, 2,6-dimethylheptyl, 2,6-dimethyl-1-heptenyl, 2,6-dimethyl-5-heptenyl and 2,6-dimethyl-1,5-heptadienyl groups.

Those exemplified more preferably are hydrocarbon groups each having 3 to 4 carbon atoms with which the melanin production inhibiting effect becomes especially high, such as n-propyl, n-butyl, isopropyl, isobutyl, sec-butyl, tert-butyl, allyl, 1-propenyl, isopropenyl, 1-butenyl, 2-butenyl, 3-butenyl, 2-methyl-1-propenyl, 2-methyl-2-propenyl, 1-ethyl-1-ethenyl, 1-methyl-1-propenyl, 1-methyl-2-propenyl groups and the like.

Most preferably, $R^2$ is selected from n-propyl, n-butyl, isobutyl, se-butyl, 1-propenyl, 1-butenyl, 2-butenyl, 3-butenyl and 2-methyl-1-propenyl groups.

$R^3$ in Compound (2) employed as a melanin production inhibitor according to the invention may be, for example selected from, but is not limited to, ethyl, n-propyl, n-butyl, isopropyl, isobutyl, sec-butyl, tert-butyl, allyl groups and the like.

Preferred examples of a compound employed as a melanin production inhibitor and/or a fragrance fixative according to the invention are, but are not limited to, the following compounds.

Compound (1) of the invention can be classified into one of the 4 types represented by the following structures (1)-1, (1)-2, (1)-3

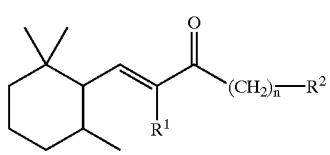

(1)-1

-continued

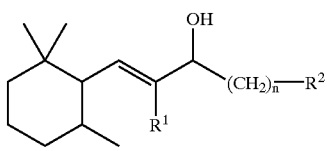 (1)-2

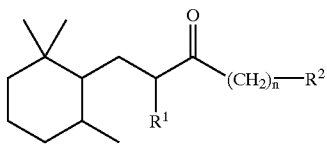 (1)-3

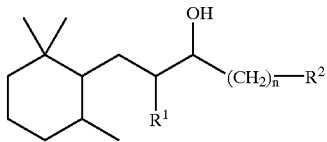 (1)-4 and (1)-4.

| Compound No. | Formula type | R¹ | R² |
|---|---|---|---|
| 1'i | (1)-1 | H | n-Propyl |
| 1"i | (1)-2 | H | n-Propyl |
| 1³'i | (1)-3 | H | n-Propyl |
| 1⁴'i | (1)-4 | H | n-Propyl |
| 1'j | (1)-1 | H | n-Butyl |
| 1"j | (1)-2 | H | n-Butyl |
| 1³'j | (1)-3 | H | n-Butyl |
| 1⁴'j | (1)-4 | H | n-Butyl |
| 1'k | (1)-1 | H | 2-Methylpropyl |
| 1"k | (1)-2 | H | 2-Methylpropyl |
| 1³'k | (1)-3 | H | 2-Methylpropyl |
| 1⁴'k | (1)-4 | H | 2-Methylpropyl |
| 1'l | (1)-1 | H | 2-Methyl-1-propenyl |
| 1"l | (1)-2 | H | 2-Methyl-1-propenyl |
| 1³'l | (1)-3 | H | 2-Methyl-1-propenyl |
| 1⁴'l | (1)-4 | H | 2-Methyl-1-propenyl |
| 1'm | (1)-1 | H | n-Pentyl |
| 1"m | (1)-2 | H | n-Pentyl |
| 1³'m | (1)-3 | H | n-Pentyl |
| 1⁴'m | (1)-4 | H | n-Pentyl |
| 1'n | (1)-1 | H | n-Hexyl |
| 1"n | (1)-2 | H | n-Hexyl |
| 1³'n | (1)-3 | H | n-Hexyl |
| 1⁴'n | (1)-4 | H | n-Hexyl |
| 1'o | (1)-1 | H | n-Heptyl |
| 1"o | (1)-2 | H | n-Heptyl |
| 1³'o | (1)-3 | H | n-Heptyl |
| 1⁴'o | (1)-4 | H | n-Heptyl |
| 1'p | (1)-1 | H | n-Octyl |
| 1"p | (1)-2 | H | n-Octyl |
| 1³'p | (1)-3 | H | n-Octyl |
| 1⁴'p | (1)-4 | H | n-Octyl |
| 1'q | (1)-1 | H | n-Nonyl |
| 1"q | (1)-2 | H | n-Nonyl |
| 1³'q | (1)-3 | H | n-Nonyl |
| 1⁴'q | (1)-4 | H | n-Nonyl |
| 1'r | (1)-1 | H | n-Decyl |
| 1"r | (1)-2 | H | n-Decyl |
| 1³'r | (1)-3 | H | n-Decyl |
| 1⁴'r | (1)-4 | H | n-Decyl |
| 1's | (1)-1 | H | 2,6-Dimethylheptyl |
| 1"s | (1)-2 | H | 2,6-Dimethylheptyl |
| 1³'s | (1)-3 | H | 2,6-Dimethylheptyl |
| 1⁴'s | (1)-4 | H | 2,6-Dimethylheptyl |
| 1't | (1)-1 | H | 2,6-Dimethyl-1,5-heptadienyl |
| 1"t | (1)-2 | H | 2,6-Dimethyl-1,5-heptadienyl |
| 1³'t | (1)-3 | H | 2,6-Dimethyl-1,5-heptadienyl |
| 1⁴'t | (1)-4 | H | 2,6-Dimethyl-1,5-heptadienyl |
| 1'x | (1)-1 | Me | n-Propyl |

-continued

| Compound No. | Formula type | R¹ | R² |
|---|---|---|---|
| 1"x | (1)-2 | Me | n-Propyl |
| 1³'x | (1)-3 | Me | n-Propyl |
| 1⁴'x | (1)-4 | Me | n-Propyl |
| 1'y | (1)-1 | Me | n-Butyl |
| 1"y | (1)-2 | Me | n-Butyl |
| 1³'y | (1)-3 | Me | n-Butyl |
| 1⁴'y | (1)-4 | Me | n-Butyl |
| 1'z | (1)-1 | Me | 2-Methylpropyl |
| 1"z | (1)-2 | Me | 2-Methylpropyl |
| 1³'z | (1)-3 | Me | 2-Methylpropyl |
| 1⁴'z | (1)-4 | Me | 2-Methylpropyl |

In addition to Compound (1) of the invention described above, preferred examples of Compound (2) used as an inventive melanin production inhibitor are, but are not limited to, the following compounds.

Similar to Compound (1), Compound (2) can also be classified into one of 4 types represented by the following structures (2)-1, (2)-2, (2)-3 and (2)-4.

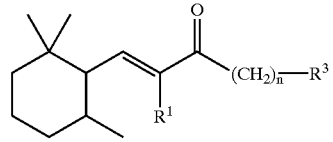 (2)-1

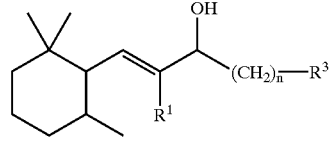 (2)-2

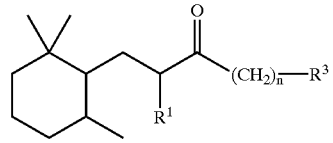 (2)-3

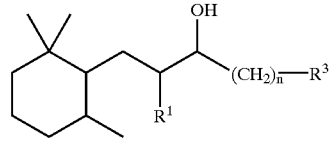 (2)-4

| Compound No. | Formula type | R¹ | R³ |
|---|---|---|---|
| 1'b | (2)-1 | H | Ethyl |
| 1"b | (2)-2 | H | Ethyl |
| 1³'b | (2)-3 | H | Ethyl |
| 1⁴'b | (2)-4 | H | Ethyl |
| 1'c | (2)-1 | H | n-Propyl |
| 1"c | (2)-2 | H | n-Propyl |
| 1³'c | (2)-3 | H | n-Propyl |
| 1⁴'c | (2)-4 | H | n-Propyl |
| 1'd | (2)-1 | H | Allyl |
| 1"d | (2)-2 | H | Allyl |
| 1³'d | (2)-3 | H | Allyl |
| 1⁴'d | (2)-4 | H | Allyl |
| 1'e | (2)-1 | H | iso-Propyl |
| 1"e | (2)-2 | H | iso-Propyl |
| 1³'e | (2)-3 | H | iso-Propyl |
| 1⁴'e | (2)-4 | H | iso-Propyl |

-continued

| Compound No. | Formula type | R¹ | R³ |
|---|---|---|---|
| 1'f | (2)-1 | H | n-Butyl |
| 1"f | (2)-2 | H | n-Butyl |
| 1³'f | (2)-3 | H | n-Butyl |
| 1⁴'f | (2)-4 | H | n-Butyl |
| 1'g | (2)-1 | H | iso-Butyl |
| 1"g | (2)-2 | H | iso-Butyl |
| 1³'g | (2)-3 | H | iso-Butyl |
| 1⁴'g | (2)-4 | H | iso-Butyl |
| 1'h | (2)-1 | H | tert-Butyl |
| 1"h | (2)-2 | H | tert-Butyl |
| 1³'h | (2)-3 | H | tert-Butyl |
| 1⁴'h | (2)-4 | H | tert-Butyl |
| 1'u | (2)-1 | Me | Ethyl |
| 1"u | (2)-2 | Me | Ethyl |
| 1³'u | (2)-3 | Me | Ethyl |
| 1⁴'u | (2)-4 | Me | Ethyl |
| 1'v | (2)-1 | Me | n-Propyl |
| 1"v | (2)-2 | Me | n-Propyl |
| 1³'v | (2)-3 | Me | n-Propyl |
| 1⁴'v | (2)-4 | Me | n-Propyl |
| 1'w | (2)-1 | Me | n-Butyl |
| 1"w | (2)-2 | Me | n-Butyl |
| 1³'w | (2)-3 | Me | n-Butyl |
| 1⁴'w | (2)-4 | Me | n-Butyl |

Compounds (1)-1, (1)-2, (1)-3 and (1)-4 represented by Formula (1) according to the invention can be, for example, synthesized as illustrated in the following schemes.

In the following schemes, $R^1$ represents hydrogen or a methyl group and $R^2$ represents a straight or branched, saturated or unsaturated hydrocarbon group having 3 to 10 carbon atoms.

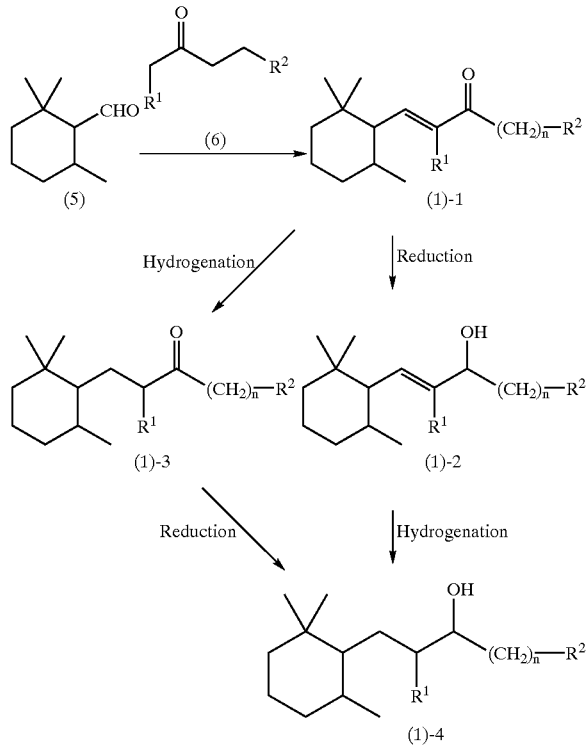

Thus, 2,2,6-trimethylcyclohexane carbaldehyde (5) and a corresponding ketone ($R^1$—$CH_2$—CO—$CH_2$—$CH_2$—$R^2$) are subjected to an aldol condensation under a known condition to obtain a 1-(2',2',6'-trimethylcyclohexan-1'-yl)pentan-1-en-3-one derivative represented by Formula (1)-1, which is subjected to a reduction using a known reducing agent to obtain a 1-(2',2',6'-trimethylcyclohexan-1'-yl)pentan-1-en-3-ol derivative represented by Formula (1)-2, which is then subjected to a hydrogenation using a known hydrogenation catalyst to obtain a 1-(2',2',6'-trimethylcyclohexan- 1'-yl)pentan-3-ol derivative represented by Formula (1)-4. Alternatively, a 1-(2',2',6'-trimethylcyclohexan-1'-yl)pentan-1-en-3-one derivative represented by Formula (1)-1 is subjected to a hydrogenation using a known hydrogenation catalyst described above to obtain a 1-(2',2',6'-trimethylcyclohexan-1'-yl)pentan-3-one derivative represented by Formula (1)-3, which is then subjected to a reduction using a known reducing agent described above to obtain a 1-(2',2',6'-trimethylcyclohexan-1'-yl)pentan-3-ol derivative represented by Formula (1)-4.

A starting material, Compound (5), can be synthesized by a known citronellal cyclization (JP-A-63-44544) or a methoxycitroneral cyclization (JP-A-4-21642). Alternatively, it can also be available by hydrogenating the double bond of cyclocitral.

A method for synthesizing a compound of Formula (1) of the invention is further detailed below.

An aldol condensation between 2,2,2-trimethylcyclohexane carbaldehyde (5) and a corresponding ketone ($R^1$—$CH_2$—CO—$CH_2$—$CH_2$—$R^2$) can be conducted using an ordinary condition as it is.

Abase employed in this reaction may be, for example, an alkaline metal hydride, an alkaline earth metal hydride, an alkaline metal hydroxide or alkoxide, an alkaline earth metal hydroxide or alkoxide oranalkalinemetalamide. Preferably employed are potassium hydride, sodium hydride, lithium hydride, calcium hydride, potassium methoxide, potassium t-butoxide, potassium hydroxide, sodium hydroxide, sodium methoxide, lithium methoxide, calcium hydroxide, barium hydroxide, sodium amide, lithium amide and lithium diisopropylamide. More preferably, potassium hydroxide, potassium methoxide, sodium hydroxide and sodium methoxide are employed.

The amount of a base used ranges from 1/1000 to 10 parts by mole based on a ketone as a reaction substrate, preferably 1/10 to 5 parts by mole.

The reaction temperature ranges from 0 to 150° C., preferably 20 to 100° C. The reaction time is preferably 1 to 20 hours. While the amount of a solvent is not particularly limited, it is preferably 0 to 20 parts based on a reaction substrate. Such solvent may be, for example, an alcohol such as methanol and ethanol, an aromatic hydrocarbon such as benzene, toluene and xylene, an aliphatic hydrocarbon such as hexane and heptane, and an ether such as diisopropylether and tetrahydrofuran.

The reduction of a 1-(2',2',6'-trimethylcyclohexan-1'-yl)pentan-1-en-3-one derivative represented by Formula (1)-1 or a 1-(2',2',6'-trimethylcyclohexan-1'-yl)pentan-3-one derivative represented by Formula (1)-3 can be conducted using an ordinary reducing condition as it is.

A reducing agent may be, for example, a metal hydride such as sodium borohydride and lithium aluminum hydride. The amount of a reducing agent to be used ranges from 1 to 10 parts based on a reaction substrate, preferably 1 to 2 parts. The reaction temperature ranges from −50 to 100° C., preferably 0 to 50° C. The reaction time is preferably 1 to 20 hours. While the amount of a solvent is not particularly limited, it is 0 to 20 parts based on a reaction substrate, preferably 1 to 10 parts. Such solvent maybe, for example, an alcohol such as methanol and ethanol, an aromatic hydrocarbon such as benzene, toluene and xylene, an aliphatic hydrocarbon such as hexane and heptane, and an ether such as diisopropylether and tetrahydrofuran.

The hydrogenation of a 1-(2',2',6'-trimethylcyclohexan-1'-yl)pentan-1-en-3-ol derivative represented by Formula (1)-2 or a 1-(2',2',6'-trimethylcyclohexan-1'-yl)pentan-1-en-3-one derivative represented by Formula (1)-1 can be conducted using an ordinary hydrogenation condition as it is.

A hydrogenation catalyst may be, for example, a metal powder itself such as nickel, palladium, rhodium, ruthenium, iridium and platinum, a heterogeneous metal catalyst adsorbed on a support such as a carbon powder, an alumina powder or a silica gel powder, or a homogeneous organic metal catalyst such as a rhodium-phosphine catalyst including a Wilkinson complex or a ruthenium-phosphine catalyst including an ikariya type complex. The amount of a catalyst to be used is 0.01 to 20% by weight based on a reaction substrate, preferably 0.1 to 5% by weight. The reaction temperature is 0 to 200° C., preferably 20 to 100° C. The hydrogen pressure is 1 to 200 kg/cm², preferably 1 to 100 kg/cm². The reaction time is preferably 1 to 20 hours. While the amount of a solvent is not particularly limited, it is 0 to 20 parts based on a reaction substrate, preferably 1 to 5 parts. Such solvent may be, for example, an alcohol such as methanol and ethanol, an aromatic hydrocarbon such as benzene, toluene and xylene, an aliphatic hydrocarbon such as hexane and heptane, an ether such as diisopropylether and tetrahydrofuran, and an ester such as ethyl acetate and butyl acetate.

Compound (1) of the invention exists as the (R, S) forms with regard to the 1' position on a cyclohexane ring where a substitution with a side chain occurs and the (R, S) forms with regard to the 6' position where a substitution with a methyl group occurs, as well as the (R, S) forms with regard to the 3 position when a side chain functionality is an alcohol and the (R, S) forms with regard to the asymmetric carbon atom as a result of a branching of the side chain, thus presenting two or more isomers including optical isomers, and any of the isomers and the mixtures thereof may be employed in the invention.

A melanin production inhibitor of the invention contains as an essential component a trimethylcyclohexane derivative which is Compound (1) of the invention represented by Formula (1):

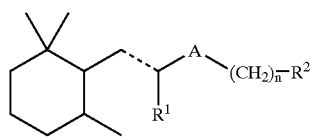

(1)

wherein A represents C=O or CH—OH, n represents 2, $R^1$ represents hydrogen or a methyl group, $R^2$ represents a straight or branched, saturated or unsaturated hydrocarbon group having 3 to 10 carbon atoms, and a dotted line represents a saturated or unsaturated carbon-carbon bond. Furthermore, a melanin production inhibitor of the invention may contain as an essential component a trimethylcyclohexane derivative which is Compound (2) represented by Formula (2):

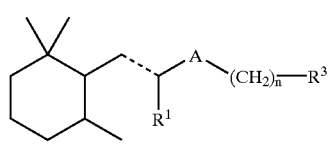

(2)

wherein A represents C=O or CH—OH, n represents 0, $R^1$ represents hydrogen or a methyl group, $R^3$ represents a straight or branched, saturated or unsaturated hydrocarbon group having 2 to 4 carbon atoms, and a dotted line represents a saturated or unsaturated carbon-carbon bond.

A fragrance fixative of the invention contains as an essential component a trimethylcyclohexane derivative which is Compound (1) of the invention represented by Formula (1):

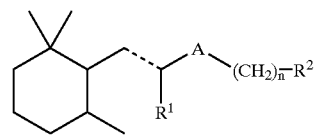

(1)

wherein A represents C=O or CH—OH, n represents 2, $R^1$ represents hydrogen or a methyl group, $R^2$ represents a straight or branched, saturated or unsaturated hydrocarbon group having 3 to 10 carbon atoms, and a dotted line represents a saturated or unsaturated carbon-carbon bond.

In addition to such essential component, ketones, aldehydes, esters, alcohols, terpenes, naturally occurring essential oils and other customary fragrances may also be combined in a formulation.

Also by employing a combination of two or more of inventive Compounds (1), the effects of the desirable aroma characteristics and fragrance fixative may further be promoted.

In the invention, a melanin production inhibitor and/or a fragrance fixative may also be contained in a dosage form to give a dermal formulation.

A dermal formulation includes a cosmetic, a pharmaceutical and a designated pharmaceutical, and its dosage form may be selected from those employed usually for a cosmetic, a pharmaceutical and a designated pharmaceutical, such as a lotion, a milky lotion, a facial pack, a foundation, a cream, an ointment, a bath salt, a gel and the like.

While the concentration of a melanin production inhibitor in a dermal dosage form may vary depending on the type of the base employed, other concomitant melanin production inhibitors, if any, and the purpose of the use, it is preferably 0.00001 to 10% by weight based on the total amount of the formulation, more preferably 0.0001 to 5% by weight.

While the concentration of a fragrance fixative in a dermal dosage form may vary depending on the type of the base employed, other concomitant fragrance fixatives, if any, and the purpose of the use, it is preferably 0.00001 to 10% by weight based on the entire amount of the formulation, more preferably 0.0001 to 5% by weight.

A base for a dermal formulation may be any known base for a dermal formulation and is not particularly limited provided that it is inert to a compound of the invention, and may be a solid, a liquid, an emulsion, a foam, a gel and the like.

A dermal formulation of the invention may contain various components employed customarily in a pharmaceutical or a cosmetic such as aqueous components, oily components, powder components, surfactants, humectants, lower or polyhydric alcohols, tackifiers, colorants, flavors, fragrance, antioxidants, pH modifiers, chelating agents, preservatives, UV protecting agents, emulsifiers, anti-inflammatory agents, pharmacologically active components, dermal nutrition supplements and the like, unless the melanin production inhibiting effect, the aroma characteristics and the fragrance fixative of an inventive compound are affected adversely.

In addition to these components, one or more other whitening components maybe incorporated, such as pantetheine-sec-sulfonic acid, isoferulic acid, ascorbic acid and derivatives thereof, arbutin, kojic acid, linolic acid, ellagic acid, glycyrrhetinic acid, a licorice extract and the like, for the purpose of further enhancing the effect.

In addition to these components, one or more other fragrance fixatives may also be incorporated, and dipropylene glycol, benzyl benzoate, trimethyl citrate and diethyl phthalate may be used concomitantly.

DETAILED DESCRIPTION OF THE INVENTION

The present invention is further described in the following examples which are not intended to restrict the invention. The instruments and the conditions employed in the examples are as follows.

(1) Gas chromatograph (Determination of % conversion);
- Instrument: HP-5890A (manufactured by Hewlett Packard Inc.)
- Column: Chemical bonded column OV-1 (25 m×0.25 mm) (manufactured by GL SCIENCE CO., LTD.)
- Carrier gas: Helium
- Column temperature: 100 to 220° C. (raised at 10° C./min)

(2) Infrared absorption spectrum (IR);
- Instrument: Model IR-810 (manufactured by NIPPON BUNKO KOGYO CO., LTD.)
- Method: Film method (3) 1H nuclear magnetic resonance spectrum ($^1$H-NMR);
- Instrument: Model AM-400 (400 MHz) (manufactured by BRUKER Inc.)
- Internal standard: Tetramethylsilane (4) Mass spectrum (MS);
- Instrument: M-80B Mass analyzer (Ionization voltage: 20 eV) (manufactured by Hitachi, Ltd.)

EXAMPLE 1

Synthesis of 1-(2',2',6'-Trimethylcyclohexan-1'-yl)octan-1-en-3-one (Compound 1'i)

5 g of a 28% solution of sodium methoxide in methanol was weighed into a 200 mL reaction flask, to which 10 ml of methanol was added and which was fitted with a condenser and heated on an oil bath at 110° C.

When methanol began to reflux, a mixture of 30.8 g (200 mmol) of 2,2,6-trimethylcyclohexane carbaldehyde and 30.0 g (263 mmol) of 2-heptanone was added dropwise via a dropping funnel over a period of 2 hours.

The heating under reflux was continued even after completion of the dropping, and the reaction was monitored by gas chromatography, which revealed the disappearance of 2,2,6-trimethylcyclohexane carbaldehyde which was the starting material by 8 hours after completion of the dropping.

After cooling, the reaction mixture was poured into a 5% aqueous HCl (100 ml) for quenching, and then extracted with hexane and washed in a separation funnel with a saturated aqueous solution of sodium carbonate followed by brine and then dried over anhydrous sodium sulfate.

After filtering the solid, the solvent was distilled off under reduced pressure using a rotary evaporator, and then the resultant liquid was distilled under reduced pressure to obtain 37.5 g (150 mmol) of 1-(2',2',6'-trimethylcyclohexan-1'-yl)octan-1-en-3-one (Compound 1'i). The results are shown below.

Yield: 75% bp: 120–121° C. (0.3 mmHg); IR (cm$^1$): 2950, 2920, 2860, 1695, 1670, 1625, 1455, 990. $^1$H-NMR (CDCl$_3$, δ ppm): 0.74 (d, J=6.2 Hz, 3H), 0.82 (s, 3H), 0.89 (s, 3H), 0.90 (t, J=6.9 Hz, 3H), 1.12–1.24 (m, 1H), 1.24–1.70 (m, 12H), 1.70–1.78 (m, 1H), 2.53 (t, J=7.5 Hz, 2H), 6.04 (d, J=15.8 Hz, 1H), 6.58 (dd, J=15.8 Hz, J=10.0 Hz, 1H). MS: 250 (M$^+$), 235, 207, 194, 179, 167, 151, 136, 124, 109, 95, 81, 69, 55, 41, 29.

EXAMPLE 2

Synthesis of 1-(2',2',6'-Trimethylcyclohexan-1'-yl)-7-methyloctan-1-en-3-one (Compound 1'k)

Similarly to Example 1 except for using 6-methyl-2-heptanone instead of 2-heptanone, an aldol condensation was performed. The results are shown below.

Yield: 72%; bp: 128–129° C. (0.3 mmHg); IR (cm$^{-1}$): 2950, 2920, 2860, 1695, 1670, 1625, 1455, 990. $^1$H-NMR (CDCl$_3$, δ ppm): 0.75 (d, J=6.2 Hz, 3H), 0.82 (s, 3H), 0.88 (d, J=6.6 Hz, 6H), 0.89 (s, 3H), 1.12–1.24 (m, 3H), 1.38–1.66 (m, 9H), 1.70–1.78 (m, 1H), 2.53 (t, J=7.5 Hz, 2H), 6.04 (d, J=15.8 Hz, 1H), 6.58 (dd, J=15.8 Hz, J=10.0 Hz, 1H). MS: 264 (M$^+$), 249, 221, 207, 194, 179, 161, 151, 136, 124, 109, 95, 81, 69, 55, 43.

EXAMPLE 3

Synthesis of 1-(2',2',6'-Trimethylcyclohexan-1'-yl)-7-methyloctan-1,6-dien-3-one (Compound 1'l)

Similarly to Example 1 except for using 6-methyl-5-hepten-2-one instead of 2-heptanone, an aldol condensation was performed. The results are shown below.

Yield: 76%; bp: 121–122° C. (0.3 mmHg); IR (cm$^{-1}$): 2950, 2920, 2860, 1695, 1670, 1625, 1455, 990. $^1$H-NMR (CDCl$_3$, δ ppm): 0.75 (d, J=6.2 Hz, 3H), 0.82 (s, 3H), 0.85–0.97 (m, 1H), 0.89 (s, 3H), 1.12–1.24 (m, 1H), 1.38–1.60 (m, 5H), 1.62 (br.s, 3H), 1.68 (br.s, 3H), 1.70–1.78 (m, 1H), 2.30 (q, J=7.4 Hz, 2H), 2.57 (t, J=7.5 Hz, 2H), 5.08–5.15 (m, 1H), 6.04 (d, J=15.8 Hz, 1H), 6.58 (dd, J=15.8 Hz, J=10.0 Hz, 1H). MS: 2642 (M$^+$), 247, 194, 179, 161, 151, 137, 124, 109, 95, 81, 69, 55, 43.

EXAMPLE 4

Synthesis of 1-(2',2',6'-Trimethylcyclohexan-1'-yl)-2-methyloctan-1-en-3-one (Compound1'x)

Similarly to Example 1 except for using 3-octanone instead of 2-heptanone, an aldol condensation was performed. The results are shown below.

Yield: 47%; bp: 130–131° C. (3 mmHg); IR (cm$^{-1}$): 2950, 2920, 2860, 1665, 1455. $^1$H-NMR (CDCl$_3$, δ ppm): 0.73 (d, J=6.6 Hz, 3H), 0.80 (s, 3H), 0.90 (t, J=6.9 Hz, 3H), 0.91 (s, 3H), 1.05–2.55 (m, 17H), 2.65 (dt, J=7.6, 2.7 Hz, 2H), 6.43 (dd, J=10.9, 1.3 Hz, 1H). MS: 264 (M$^+$), 249, 221, 208, 193, 179, 165, 136, 123, 109, 95, 81, 69, 55, 41.

EXAMPLE 5

Synthesis of 1-(2',2',6'-Trimethylcyclohexan-1'-yl)-decan-1-en-3-one (Compound 1'm)

Similarly to Example 1 except for using 2-nonanone instead of 2-heptanone, an aldol condensation was performed. The results are shown below.

Yield: 73%; bp: 131° C. (0.3 mmHg); IR (cm$^{-1}$): 2950, 2920, 2860, 1965, 1670, 1625, 1455, 990. $^1$H-NMR (CDCl$_3$, δ ppm): 0.74 (d, J=6.2 Hz, 3H), 0.82 (s, 3H), 0.89 (s, 3H), 0.90 (t, J=6.9 Hz, 3H), 1.12–1.70 (m, 17H), 1.70–1.78 (m, 1H), 2.53 (t, J=7.5 Hz, 2H), 6.04 (d, J=15.8 Hz, 1H), 6.58 (dd, J=15.8 Hz, J=10.0 Hz, 1H). MS: 278 (M$^+$), 263, 235, 207, 194, 179, 166, 153, 136, 124, 109, 95, 81, 69, 55, 41, 29.

EXAMPLE 6

Synthesis of 1-(2',2',6'-Trimethylcyclohexan-1'-yl)-dodecan-1-en-3-one (Compound 1'o)

Similarly to Example 1 except for using 2-undecanone instead of 2-heptanone, an aldol condensation was performed. The results are shown below.

Yield: 70%; bp: 137° C. (0.3 mmHg); IR (cm$^{-1}$): 2950, 2920, 2860, 1965, 1670, 1625, 1455, 990. $^1$H-NMR (CDCl$_3$, δ ppm): 0.74 (d, J=6.2 Hz, 3H), 0.82 (s, 3H), 0.89 (s, 3H), 0.90 (t, J=6.9 Hz, 3H), 1.12–1.70 (m, 21H), 1.70–1.78 (m, 1H), 2.53 (t, J=7.5 Hz, 2H), 6.04 (d, J=15.8 Hz, 1H), 6.58 (dd, J=15.8 Hz, J=10.0 Hz, 1H). MS: 306 (M$^+$), 291, 263, 235, 207, 194, 179, 166, 153, 136, 124, 109, 95, 81, 69, 55, 41, 29.

EXAMPLE 7

Synthesis of 1-(2',2',6'-trimethylcyclohexan-1'-yl) octan-1-en-3-ol (Compound1"i)

A 500 mL reaction flask received 300 ml of methanol and was cooled at −18° C. and then received 4.8 g (127 mmol) of sodium borohydride. After sodium borohydride was dissolved completely, 30.0 g (120 mmol) of 1-(2',2',6'-trimethylcyclohexan-1'-yl)octan-1-en-3-one (Compound 1'i) produced in Example 1 was added dropwise from a dropping funnel.

After dropping entirely, an ice bath was removed and the mixture was stirred at room temperature for 1 hour and then heated on an oil bath at 40° C.

The reaction was monitored by thin layer chromatography, which revealed the disappearance of Compound (1'i) which was the starting material after 2 hours of heating.

The reaction mixture was poured into a 5% aqueous HCl (100 ml) for quenching, and then extracted with hexane and washed in a separation funnel with an saturated aqueous solution of sodium hydrogen carbonate followed by brine and then dried over anhydrous sodium sulfate.

After filtering the solid, the solvent was distilled off under reduced pressure using a rotary evaporator, and then the resultant liquid was distilled under reduced pressure to obtain 26.7 g (106mmol) of 1-(2',2',6'-trimethylcyclohexan-1'-yl)octan-1-en-3-ol (Compound 1"i).

Yield: 88%; bp: 97–98° C. (0.3 mmHg); IR (cm$^{-1}$): 3345, 2920, 2860, 1455, 1385, 1365, 970. $^1$H-NMR (CDCl$_3$, δ ppm): 0.72–1.00 (m, 12H), 1.10–1.20 (m, 1H), 1.24–1.64 (m, 15H), 1.66–1.74 (m, 1H), 4.02–4.12 (m, 1H), 5.28–5.44 (m, 2H). MS: 252 (M$^+$), 234, 219, 181, 163, 149, 127, 109, 95, 81, 69, 55, 41, 28.

EXAMPLE 8

Synthesis of 1-(2',2',6'-Trimethylcyclohexan-1'-yl)-7-methyloctan-1-en-3-ol (Compound 1"k)

Similarly to Example 7, Compound (1',k) obtained in Example 2 was reduced. The results are shown below.

Yield: 99%; bp: 119–120° C. (0.3 mmHg); IR (cm$^{-1}$): 3345, 2920, 2860, 1455, 1385, 1365, 970. $^1$H-NMR (CDCl$_3$, δ ppm): 0.72–0.95 (m, 16H), 1.10–1.22 (m, 3H), 1.24–1.62 (m, 11H), 1.66–1.74 (m, 1H), 4.08 (q, J=6.5 Hz, 1H), 5.28–5.44 (m, 2H). MS: 266 (M$^+$), 248, 233, 209, 181, 163, 141, 125, 109, 95, 81, 69, 57, 43.

EXAMPLE 9

Synthesis of 1-(2',2',6'-Trimethylcyclohexan-1'-yl)-7-methyloctan-1,6-dien-3-ol (Compound 1"l)

Similarly to Example 7, Compound (1',l) obtained in Example 3 was reduced. The results are shown below.

Yield: 88%; bp: 128–129° C. (0.3 mmHg); IR vmax (cm$^{-1}$): 3345, 2920, 2860, 1455, 1385, 1365, 970. $^1$H-NMR (CDCl$_3$, δ ppm): 0.72–0.85 (m, 9H), 0.85–0.95 (m, 1H), 1.10–1.20 (m, 1H), 1.38–1.74 (m, 9H), 1.61 (br.s, 3H), 1.69 (br.s, 3H), 2.05 (q, J=7.4 Hz, 2H), 4.09 (q, J=6.4 Hz, 1H), 5.10–5.18 (m, 1H), 5.28–5.45 (m, 2H). MS: 264 (M$^+$), 246, 221, 179, 163, 149, 139, 124, 109, 95, 83, 69, 55, 43.

EXAMPLE 10

Synthesis of 1-(2',2',6'-Trimethylcyclohexan-1'-yl)-2-methyloctan-1-en-3-ol (Compound 1"x)

Similarly to Example 7, Compound (1',x) obtained in Example 4 was reduced. The results are shown below.

Yield: 88%; bp: 127–128° C. (3 mmHg); IR (cm$^{-1}$): 3350, 2920, 2860, 1455, 1375, 1015. $^1$H-NMR (CDCl$_3$, δ ppm): 0.72–1.05 (m, 12H), 1.10–2.25 (m, 17H), 1.59 (br.s, 3H), 4.03 (t, J=6.4 Hz, 1H), 5.12–5.18 (m, 1H). MS: 266 (M$^+$), 251, 233, 195, 177, 163, 141, 125, 109, 95, 81, 69, 55, 43, 29.

EXAMPLE 11

Synthesis of 1-(2',2',6'-Trimethylcyclohexan-1'-yl)-decan-1-en-3-ol (Compound 1"m)

Similarly to Example 7, Compound (1',m) obtained in Example 5 was reduced. The results are shown below.

Yield: 90%; bp: 114° C. (0.3 mmHg); IR (cm$^{-1}$): 3345, 2920, 2860, 1455, 1385, 1365, 970. $^1$H-NMR (CDCl$_3$, δ ppm): 0.72–1.00 (m, 12H), 1.10–1.74 (m, 21H), 4.02–4.12 (m, 1H), 5.28–5.44 (m, 2H). MS: 280 (M$^+$), 262, 247, 219, 221, 207, 181, 163, 155, 138, 125, 109, 95, 81, 69, 55, 41, 28.

EXAMPLE 12

Synthesis of 1-(2',2',6'-Trimethylcyclohexan-1'-yl)-dodecan-1-en-3-ol (Compound 1"o)

Similarly to Example 7, Compound (1',o) obtained in Example 6 was reduced. The results are shown below.

Yield: 99%; bp: 142° C. (0.3 mmHg); IR (cm$^{-1}$): 3345, 2920, 2860, 1455, 1385, 1365, 970. $^1$H-NMR (CDCl$_3$, δ ppm): 0.72–1.00 (m, 12H), 1.10–1.74 (m, 25H), 4.02–4.12 (m, 1H), 5.28–5.44 (m, 2H). MS: 308 (M$^+$), 290, 275, 247, 223, 205, 183, 163, 138, 125, 109, 95, 81, 69, 55, 41, 29.

EXAMPLE 13

Synthesis of 1-(2',2',6'-Trimethylcyclohexan-1'-yl)-octan-3-ol (Compound 1$^4$"i)

A 300 mL autoclave received 58.1 g (230 mmol) of 1-(2',2',6'-trimethylcyclohexan-1'-yl)-octane-1-en-3-ol (Compound 1"i), 60 ml of methanol and 1.45 g (2.5% wt %) of a rhodium-alumina hydrogenation catalyst, and a hydrogenation was performed at a hydrogen pressure of 100 kg/cm² and at an oil bath temperature of 100° C.

The reaction was monitored by gas chromatography, which revealed the disappearance of Compound (1"i) which was the starting material 2 hours after initiation of the reaction.

The reaction mixture was filtered with suction to remove the catalyst and the solvent was distilled off under reduced pressure using a rotary evaporator and the resultant liquid was distilled under reduced pressure to obtain 57.4 g (226 mmol) of the intended compound, 1-(2',2',6'-trimethylcyclohexan-1'-yl)-octan-3-ol (Compound $1^{4"}$i) Yield: 96% bp: 116° C. (0.3 mmHg) IR (cm¹): 3345, 2920, 2860, 1463, 1458, 1381, 1371, 1361, 1113, 978. ¹H-NMR (CDCl₃, δ ppm): 0.50–0.57 (m, 1H), 0.79 (s, 2H), 0.84–0.97 (m, 10H), 0.97–1.23 (m, 2H), 1.23–1.38 (m, 9H), 1.38–1.51 (m, 6H), 1.51–1.65 (m, 3H), 3.55 (brs, 1H). MS: 254 (M⁺), 236, 221, 207, 193, 184, 180, 165, 154, 149, 138, 123, 109, 95, 83, 69, 55, 41, 28.

EXAMPLE 14

Synthesis of 1-(2',2',6'-Trimethylcyclohexan-1'-yl)-decan-3-ol (Compound $1^{4"}$m)

Similarly to Example 13, Compound (1",m) obtained in Example 11 was hydrogenated. The results are shown below.

Yield: 95%; bp: 127° C. (0.3 mmHg); IR (cm⁻¹): 3345, 2920, 2860, 1463, 1458, 1381, 1371, 1361, 1113, 978. ¹H-NMR (CDCl₃, δ ppm): 0.50–0.57 (m, NH), 0.79 (s, 2H), 0.84–0.97 (m, 10H), 0.97–1.23 (m, 2H), 1.23–1.38 (m, 13H), 1.38–1.51 (m, 6H), 1.51–1.65 (m, 3H), 3.55 (brs, 1H). MS: 282 (M⁺), 264, 249, 221, 208, 183, 180, 154, 138, 124, 109, 95, 83, 69, 55, 41, 28.

EXAMPLE 15

Synthesis of 1-(2',2',6'-Trimethylcyclohexan-1'-yl)-dodecan-3-ol (Compound $1^{4"}$l)

Similarly to Example 13, Compound (1",o) obtained in Example 12 was hydrogenated. The results are shown below.

Yield: 94%; bp: 140° C. (0.3 mmHg); IR (cm⁻¹): 3345, 2920, 2860, 1463, 1458, 1381, 1371, 1361, 1113, 978. ¹H-NMR (CDCl₃, δ ppm): 0.50–0.57 (m, 1H), 0.79 (s, 2H), 0.84–0.97 (m, 10H), 0.97–1.23 (m, 2H), 1.23–1.38 (m, 17H), 1.38–1.51 (m, 6H), 1.51–1.65 (m, 3H), 3.55 (brs, 1H). MS: 310 (M⁺), 292, 277, 249, 236, 221, 207, 154, 138, 124, 109, 95, 83, 69, 55, 41, 28.

EXAMPLE 16

Melanin Production Inhibiting Effect on Chromatophore

A plastic culture flask (25 cm²) was inoculated with 8×10⁴ B-16 melanoma cells, which were incubated in a DMEN medium (Nippon Suisan Kaisha, Ltd.) containing 10% serum in the presence of 5% $CO_2$ at 37° C. After 3 days, a test sample diluted with EtOH was added to the medium at a concentration of 0.4, 0.8, 1.6, 3.1 and 6.2 ppm and the culture was continued for further 3 days.

After completion of the culture to remove the culture followed by washing with a phosphate buffer (hereinafter referred to as PBS), the cells were removed from the flask using a medium containing trypsin and EDTA (ethylenediamine tetraacetic acid) and the cells were recovered from the cell suspension by centrifugation.

The cells thus obtained were washed once with PBS and then the pellets were evaluated visually for their whiteness. The results are shown in Table 1.

−: Equal to solvent control (black)

+: Slightly different from solvent control (dark gray)

++: Markedly different from solvent control (pale gray)

+++: No coloring of cells (white)

TABLE 1

| sample (compound No.) | 1.6 (ppm) | 3.1 (ppm) | 6.2 (ppm) |
|---|---|---|---|
| 1'b | + | ++ | +++ |
| 1"b | + | ++ | +++ |
| 1⁴"b | + | ++ | +++ |
| 1'c | + | ++ | +++ |
| 1"c | ++ | +++ | +++ |
| 1⁴"c | + | ++ | +++ |
| 1⁴"e | + | ++ | +++ |
| 1'g | + | ++ | +++ |
| 1"g | +++ | +++ | +++ |
| 1⁴"g | ++ | +++ | +++ |
| 1'h | + | ++ | +++ |
| 1'i | +++ | +++ | +++ |
| 1"i | +++ | +++ | +++ |
| 1⁴"i | ++ | +++ | +++ |
| 1'k | ++ | +++ | +++ |
| 1"k | +++ | +++ | +++ |
| 1'l | + | +++ | +++ |
| 1"l | +++ | +++ | +++ |
| 1'm | + | + | +++ |
| 1"m | + | + | +++ |
| 1⁴"m | + | + | + |
| 1"u | + | ++ | +++ |
| 1'x | + | ++ | +++ |
| 1"x | + | ++ | +++ |

As evident from these results, any trimethylcyclohexane derivative which is a compound of the invention was proven to have a marked inhibitory effect on the production of melanin in a chromatophore when compared with the solvent control.

This inhibitory effect depends evidently on the number of the carbon atoms in the side chain of a compound, and, for example, the maximum activity at 3.1 ppm in the conjugated ketones was observed with the number of the carbon atoms in the side chain of about 5 based on a comparison among samples 1'b, 1'c, 1'i and 1'm, that in the saturated alcohols was observed with the number of the carbon atoms in the side chain of about 5 based on a comparison among samples 1⁴"b, 1⁴"c, 1⁴"i and 1⁴"m, and that among the allylalcohols was observed with the number of the carbon atoms in the side chain of about 3 to 5 based on a comparison among samples 1"b, 1"c, 1"i and 1"m.

On the bases of the type of the side chain functionality, an allylalcohol, a conjugated ketone and then a saturated alcohol exhibited higher activity in this order when evaluated visually.

A part of the data in Table 1 was extracted and is represented in Table 2 in terms of the relationship between the inhibitory effect and the number of carbon atoms in the side chain of a compound.

TABLE 2

| Compound No. | Dotted line | A | Number of carbon atoms in side chain | Concentration (ppm) 1.6 | 3.1 | 6.2 |
|---|---|---|---|---|---|---|
| 1'b | Unsaturated | CO | C2 | + | ++ | +++ |
| 1"b | Unsaturated | CH—OH | C2 | + | ++ | +++ |
| 1⁴'b | Saturated | CH—OH | C2 | + | ++ | +++ |
| 1'c | Unsaturated | CO | C3 | + | ++ | +++ |
| 1"c | Unsaturated | CH—OH | C3 | ++ | +++ | +++ |
| 1⁴'c | Saturated | CH—OH | C3 | + | ++ | +++ |
| 1'i | Unsaturated | CO | C5 | +++ | +++ | +++ |
| 1"i | Unsaturated | CH—OH | C5 | +++ | +++ | +++ |
| 1⁴'i | Saturated | CH—OH | C5 | ++ | +++ | +++ |
| 1'm | Unsaturated | CO | C7 | + | + | +++ |
| 1"m | Unsaturated | CH—OH | C7 | + | + | +++ |
| 1⁴'m | Saturated | CH—OH | C7 | + | + | + |

COMPARATIVE 1

Similarly to Example 16, the melanin production inhibiting effects of arbutin, tetrahydroionol, β-ionone, dihydro-β-ionone and the novel compounds of the invention (1'i, 1"i, 1⁴'i) on a chromatophore were determined. The results are shown in Table 3.

TABLE 3

| Compound | Concentration (ppm) 0.4 | 0.8 | 1.6 | 3.1 | 6.2 |
|---|---|---|---|---|---|
| Comparative example | | | | | |
| ARBUTIN | − | − | − | − | + |
| Tetrahydroionol | − | − | − | + | ++ |
| β-Ionone | − | − | − | + | ++ |
| Dihydro-β-ionone | − | − | − | + | ++ |
| Compound of invention (1'i) | − | + | +++ | +++ | +++ |
| Compound of invention (1"i) | − | + | +++ | +++ | +++ |
| Compound of invention (1⁴'i) | − | − | ++ | +++ | +++ |

As evident from these results, the compounds of the invention exhibited markedly potent melanin production inhibiting effects even at lower concentrations when compared with arbutin which is a representative melanin production inhibitor having an entirely different structure or with the ionone derivatives having similar structures.

EXAMPLE 17

50 mg of a lanolin paste containing 2% by weight of an inventive compound (1'i, 1'i) spread on a surgical tape for patch tests (TORII PHARMACEUTICAL CO., LTD.) was applied to an upper arm of each of 30 panelists in total consisting of males and females in their age of twenties to fifties, and after 24 hours when the surgical tape was peeled off and the further 24 hours thereafter the condition of the skin where the test substance was applied was observed and any abnormality was evaluated for the degree and the number of the panelists exhibiting such abnormality. The results are shown in Table 4.

TABLE 4

| Test substance | Number of panelists exhibiting abnormality | Number ot panelists exhibiting no abnormality |
|---|---|---|
| 1'i | 0 | 30 |
| 1"i | 0 | 30 |

EXAMPLE 18

The compounds of the invention were evaluated organoleptically by 7 trained panelists for the fragrances using scent papers, and the results shown in Table 5 were obtained.

TABLE 5

| Test substances | Quality of fragrances |
|---|---|
| Inventive compounds | |
| 1"I | Odorless |
| 1"k | Odorless |
| 1"i | Odorless |
| 1⁴'i | Very weak, siight amber scent |
| 1⁴'j | Almost odorless |
| 1⁴'m | Odorless |
| 1⁴'n | Odorless |
| 1⁴'o | Odorless |
| Comparative compounds | |
| Tetrahydroionol | Dry and woody scent |
| β-Ionone | Sweet and potently woody floral scent |
| Dihydro-β-ionone | Amber-nuanced woody floral scent |

COMPARATIVE 2

Similarly to Example 18, the fragrances of tetrahydroionol, β-ionone and dihydro-β-ionone as the comparative compounds were evaluated, and the results shown in Table 5 were obtained.

As evident from Table 5, the compounds of the invention which are odorless unlike the comparative compounds having lower molecular weights do not adversely affect the aroma of a fragrance incorporated into a dermal formulation.

EXAMPLE 19

The components of each of the oil phase and the water phase shown in the following table were dissolved at room temperature with stirring. The water phase was combined with the oil phase and solubilized to form a lotion. The amounts of the components of the oil and water phases are represented by % by weight.

| <Oil phase> | |
|---|---|
| 1-(2',2',6'-trimethylcyclohexan-1'-yl)octan-1-en-3-one (Compound 1'i) | 0.01 |
| Ethanol | 20.0 |
| polyoxyethylene-hardened castor oil (50EO) | 0.05 |
| Methyl p-oxybenzoate | 0.1 |
| Fragrance | 0.1 |

-continued

| <Water phase> | |
|---|---|
| Glycerin | 10.0 |
| 1,3-Butylene glycol | 5.0 |
| Purified water | Balance |

The lotion obtained had a higher whitening effect when compared with a formulation containing no inventive compound and a satisfactory fixative stability.

EXAMPLE 20

The components of each of the oil phase and the water phase shown in the following table were dissolved at room temperature with stirring. The water phase was combined with the oil phase and solubilized to form an emulsion. The amounts of the components of the oil and water phases are represented by % by weight.

| <Oil phase> | |
|---|---|
| (2',2',6'-trimethylcyclohexan-1'-yl) octan-1-en-3-ol (Compound 1"i) | 0.1 |
| Stearic acid | 2.0 |
| Liquid paraffin | 6.0 |
| Squarene | 2.0 |
| Sorbitan monostearate | 1.5 |
| Polyoxyethylene sorbitan monostearate (20EO) | 2.0 |
| Butyl p-oxybenzoate | 0.05 |
| Methyl p-oxybenzoate | 0.1 |
| Fragrance | 0.15 |
| <Water phase> | |
| Glycerin | 5.0 |
| 1,3-Butylene glycol | 5.0 |
| Purified water | Balance |

The emulsion obtained had a higher whitening effect when compared with a formulation containing no inventive compound and a satisfactory fixative stability.

EXAMPLE 21

The components of each of the oil phase and the water phase shown in the following table were dissolved at 70° C. with stirring. The water phase was combined portionwise with the oil phase with stirring to effect a preliminary emulsification and then emulsified uniformly using a homomixer, and then cooled to 30° C. with stirring sufficiently, whereby obtaining a cream. The amounts of the components of the oil and water phases are represented by % by weight.

| <Oil phase> | |
|---|---|
| 1-(2',2',6'-trimethylcyclohexan-1'-yl) octan-3-ol (Compound 1<sup>4</sup>"i) | 0.1 |
| Stearic acid | 2.0 |
| Liquid paraffin | 23.0 |
| Vaseline | 7.0 |
| Sorbitan monostearate | 3.5 |
| Beeswax | 2.0 |
| Behenyl alcohol | 1.0 |
| Polyoxyethylene sorbitan monostearate (20EO) | 2.5 |
| Butyl p-oxybenzoate | 0.05 |

-continued

| Methyl p-oxybenzoate | 0.1 |
|---|---|
| Fragrance | 0.15 |
| <Water phase> | |
| Glycerin | 5.0 |
| 1,3-Butylene glycol | 5.0 |
| Purified water | Balance |

The cream obtained had a higher whitening effect when compared with a formulation containing no inventive compound and a satisfactory fixative stability.

EXAMPLE 22

Expression Test of Neat Fragrance

Each of methylnonylketone (A) and n-decylaldehyde (B) was subjected to an expression test.

Each of the neat fragrances A and B was mixed uniformly with each of the three fixatives and Compound (1"i) shown in Table 6 in a weight ratio of 1:1 each in the amount of 100 mg, and about 10.0 mg of the mixture was weighed onto a filter paper placed on the bottom of a broad-necked bottle of 40 mm in diameter and 50 mm in height, which was allowed to stand with being closed with a lid for 30 minutes and then used as an evaluation sample.

Separately, 5.0 mg of each neat fragrance was weighed to obtain a fixative-free sample for the evaluation.

10 trained panelists having the experiences of 5 years or longer evaluated the expression of the fragrance immediately after opening the bottle on the basis of the following evaluation scores, and the total of the scores of the 10 panelists was used as a rating.

Ratings: More intense than fixative-free sample: 2
No difference from fixative-free sample: 1
Less intense than fixative-free sample: 0
The results are shown in Table 6.

TABLE 6

Fragrance expression test

| Evaluation sample | | |
|---|---|---|
| Fragrance | Retainer | Rating |
| Methylnonylketone | Dipropylene glycol | 8 |
| " | Triethyl citrate | 8 |
| " | Benzyl benzoate | 7 |
| " | Inventive compound(1"i) | 13 |
| n-Decylaldehyde | Dipropylene glycol | 9 |
| " | Triethyl citrate | 8 |
| " | Benzyl benzoate | 8 |
| " | Inventive compound(1"i) | 12 |

EXAMPLE 23

Fixative Test of Neat Fragrance

Each of methylnonylketone (A), n-decylaldehyde (B) and ethyl octanoate (C) was. subjected to a fixative test.

Each of the neat fragrances A, B and C was mixed uniformly with each of the three fixatives and Compound (1"i) shown in Table 7 in a weight ratio of 1:1 each in the amount of 100 mg similarly to Example 22, and about 10.0 mg of the mixture was weighed onto a filter paper placed on the bottom of a broad-necked bottle of 40 mm in diameter and 50 mm in height, which was allowed to stand without being closed with a lid at room temperature for about 8 hours and then used as an evaluation sample.

Separately, 5.0 mg was weighed to obtain a fixative-free sample for the evaluation.

The evaluation was conducted similarly to Example 22. 10 trained perfumer panelists compared the intensity of the retained fragrance between the fixative-containing and fixative-free samples, and the following scores were employed to obtain the total of the scores of the 10 panelists which was used as a rating.

Ratings: More intense than fixative-free sample: 2
No difference from fixative-free sample: 1
Less intense than fixative-free sample: 0
The results are shown in Table 7.

TABLE 7

Fragrance fixative test

| Evaluation sample | | |
|---|---|---|
| Fragrance | Retainer | Rating |
| Methylnonylketone | Dipropylene glycol | 10 |
| " | Triethyl citrate | 13 |
| " | Benzyl benzoate | 16 |
| " | Inventive compound (1"i) | 20 |
| n-Decylaldehyde | Dipropylene glycol | 7 |
| " | Triethyl citrate | 8 |
| " | Benzyl benzoate | 7 |
| " | Inventive compound (1"i) | 15 |
| Ethyl octanoate | Dipropylene glycol | 8 |
| " | Triethyl citrate | 11 |
| " | Benzyl benzoate | 13 |
| " | Inventive compound (1"i) | 16 | tion 2 and Comparative formulation 3 were prepared and subjected to the expression test and the fixative test.

About 10.0 mg of each fragrance composition was weighed onto a filter paper placed on the bottom of a broad-necked bottle of 40 mm in diameter and 50 mm in height, which was allowed to stand with being closed with a lid for 30 minutes to obtain an evaluation sample, which was evaluated for the expression immediately after opening the bottle, and then for the fixative after being allowed to stand without being closed with a lid for about 8 hours.

10 trained perfumer panelists having the experiences of 5 years or longer evaluated a sample three times repetitively (30 panelists in total) and the intensity relative to Comparative formulation 3 was evaluated.

The results are shown in Table 8.

Table 8 shows the number of the panelists who felt the expression most eminently when compared with Comparative formulation 3. The rating "3" assigned to Comparative formulation 3 means that no difference was noted. The number of the panelists who felt the fixative most clearly when compared with Comparative formulation 3 is also indicated. The rating "3" assigned to Comparative formulation 3 means that no difference was noted.

TABLE 8

Fragrance expression and fixative tests

| | Fragrance compositions | | | | |
|---|---|---|---|---|---|
| Components | Formulation A | Formulation B | Comparative formulation 1 | Comparative formulation 2 | Comparative formulation 3 |
| n-Decylaldehyde | 1 | 1 | 1 | 1 | 1 |
| Citronellal | 6 | 6 | 6 | 6 | 6 |
| L-Citronellal | 15 | 15 | 15 | 15 | 15 |
| α-DAMASCONE | 1 | 1 | 1 | 1 | 1 |
| Geranyl acetate | 6 | 6 | 6 | 6 | 6 |
| L-Laurinal | 20 | 20 | 20 | 20 | 20 |
| Methylheptenone | 1 | 1 | 1 | 1 | 1 |
| Methylionone | 10 | 10 | 10 | 10 | 10 |
| Orange Oil | 10 | 10 | 10 | 10 | 10 |
| Phenylethyl alcohol | 25 | 25 | 25 | 25 | 25 |
| Inventive compound (1"i) | 5 | 2 | — | — | — |
| Inventive compound (1'm) | — | 1 | — | — | — |
| Inventive compound (1⁴"o) | — | 1 | — | — | — |
| Triethyl citrate | — | — | 5 | — | — |
| Dipropylene glycol | — | — | — | 5 | — |
| Fragrance expression ratings | 10 | 13 | 1 | 3 | 3 |
| Fragrance fixative ratings | 9 | 16 | 2 | 0 | 3 |

EXAMPLE 24

Expression and Fixative Tests of Fragrance Composition

In accordance with the formulations shown in Table 8, the fragrance compositions including Formulation A, Formulation B, Comparative formulation 1, Comparative formulation 2 and Comparative formulation 3 were prepared and subjected to the expression test and the fixative test.

The amount of each component is represented in grams.

Based on the results described above, a compound of the invention is proven to be excellent in terms of both of the fragrance expression and the fragrance fixative when added also to a formulated fragrance described above, and a combination of the compounds of the invention gave more excellent results.

Industrial Applicability

According to the invention, a novel trimethylcyclohexane derivative useful as a melanin production inhibitor and a fragrance fixative is provided. Also provided is a novel melanin production inhibitor which has a higher melanin production inhibiting effect and excellent stability and safety without affecting a product fragrance adversely as well as a novel fragrance fixative capable of promoting the expression and the fixative of a fragrance markedly. Also when a melanin production inhibitor is incorporated into a dermal formulation, it exhibits an extremely high stability in a formulation or in a base and is stable, thus providing a dermal formulation having a satisfactory whitening effect.

What is claimed is:

1. A trimethylcyclohexane derivative represented by Formula (1):

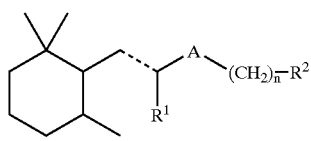

(1)

wherein A represents C=O or CH—OH, n represents 2, $R^1$ represents hydrogen or a methyl group, $R^2$ represents a straight or branched, saturated or unsaturated hydrocarbon group having 3 to 10 carbon atoms, and a dotted line represents a saturated or unsaturated carbon-carbon bond.

2. A trimethylcyclohexane derivative according to claim 1 represented by Formula (1):

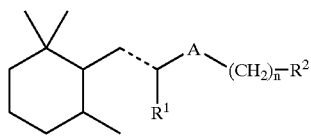

(1)

wherein $R^2$ is selected from the group consisting of n-propyl, n-butyl, n-pentyl, n-hexyl, n-heptyl, isopropyl, isobutyl, sec-butyl, tert-butyl, allyl, 1-propenyl, isopropenyl, 1-butenyl, 2-butenyl, 3-butenyl, 2-methyl-1-propenyl, 2-methyl-2-propenyl, 1-ethyl-1-ethenyl, 1-methyl-1-propenyl, 1-methyl-2-propenyl, 1-methyl-2-propenyl, 2,6-dimethylheptyl, 2,6-dimethyl-1-heptenyl, 2,6-dimethyl-5-heptenyl and 2,6-dimethyl-1,5-heptadienyl groups.

3. A trimethylcyclohexane derivative according to claim 1 represented by Formula (1):

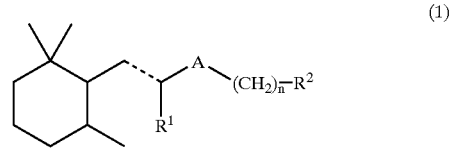

(1)

wherein $R^2$ is selected from the group consisting of n-propyl, n-butyl, isopropyl, isobutyl, sec-butyl, tert-butyl, allyl, 1-propenyl, isopropenyl, 1-butenyl, 2-butenyl, 3-butenyl, 2-methyl-1-propenyl, 2-methyl-2-propenyl, 1-ethyl-1-ethenyl, 1-methyl-1-propenyl and 1-methyl-2-propenyl groups.

4. A melanin production inhibitor comprising one or more of trimethylcyclohexane derivatives according to claim 1.

5. A fragrance fixative comprising one or more of trimethylcyclohexane derivatives according to claim 1.

6. A dermal formulation comprising one or more melanin production inhibitors according to claim 4.

7. A melanin production inhibitor comprising one or more of trimethylcyclohexane derivatives according to claim 2.

8. A melanin production inhibitor comprising one or more of trimethylcyclohexane derivatives according to claim 3.

9. A fragrance fixative comprising one or more of trimethylcyclohexane derivatives according to claim 2.

10. A fragrance fixative comprising one or more of trimethylcyclohexane derivatives according to claim 3.

11. A dermal formulation comprising one or more fragrance fixatives according to claim 5.

12. A dermal formulation comprising one or more melanin production inhibitors according to claim 7.

13. A dermal formulation comprising one or more melanin production inhibitors according to claim 8.

14. A dermal formulation comprising one or more fragrance fixatives according to claim 9.

15. A dermal formulation comprising one or more fragrance fixatives according to claim 10.

* * * * *